(12) United States Patent
Itoh et al.

(10) Patent No.: US 7,098,245 B2
(45) Date of Patent: Aug. 29, 2006

(54) POLYNUCLEOTIDE CLEAVAGE AGENT SWITCHED ON BY PHOTO IRRADIATION

(75) Inventors: Toshiyuki Itoh, Tottori-ken (JP); Keiko Ninomiya, Okayama-ken (JP); Masahiko Shishido, Okayama-ken (JP)

(73) Assignee: Tottori University, Tottori (JP)

( * ) Notice: Subject to any disclaimer, the term of this patent is extended or adjusted under 35 U.S.C. 154(b) by 450 days.

(21) Appl. No.: 10/378,647

(22) Filed: Mar. 5, 2003

(65) Prior Publication Data

US 2004/0058346 A1 Mar. 25, 2004

(30) Foreign Application Priority Data

Sep. 6, 2002 (JP) ............................. 2002-261529

(51) Int. Cl.
*A01N 53/00* (2006.01)
*C12Q 1/68* (2006.01)
*C07H 21/00* (2006.01)
(52) U.S. Cl. ......................... 514/531; 560/124; 435/6; 536/23.1
(58) Field of Classification Search ................... 435/6; 536/23.1; 514/531; 560/124
See application file for complete search history.

(56) References Cited

OTHER PUBLICATIONS

Ly, D. et al, J. Am. Chem Soc. 118, 8747-8748 (1996).
Kumar, C.V. et al, Tetrahedron, 56, 7027-7040 (2000).
Toshima, K et al, Bioorganic & Medicinal Chemistry Letters 10, 2163-2165 (2000).
Toshima, K. et al, Chem. Commun. 3, 212-213 (2002).
Itoh, T. et al, "Synthesis of gem-Difluorocyclopropane Derivatives and Investigation on their DNA cleavage Property", 81st Annual Meeting of the Chemical Society of Japan, 2002 (Mar. 11, 2002).
Itoh, T. et al "Synthesis of gem-Difluorocyclopropane Derivatives and Investigation on their Bioactivities" Abstracts of the 25th Flourine Conference of Japan (Nov. 18-20, 2001).

*Primary Examiner*—Jezia Riley
(74) *Attorney, Agent, or Firm*—Bacon & Thomas, PLLC

(57) ABSTRACT

The present invention provides a polynucleotide cleavage agent switched on by photo-irradiation and a method of cleaving or decomposing a polynucleotide such as DNA or RNA using this agent switched on in this manner. More specifically, said polynucleotide cleavage agent switched on by photo-irradiation comprises cyclopropane or a 2,2-dihalogeno-cyclopropane ring between "A" unit and "B" unit, wherein said "A" unit is an aromatic group having an electron withdrawing property and is excited by photo-irradiation, and said "B" unit is a hydrophilic functional group. Said polynucleotide cleavage agent may further contain "C" unit which can recognize DNA sequences, and also a spacer molecule, if desired.

20 Claims, 4 Drawing Sheets

Model compound 1: For no site specific cleavage

Model compound 2: For site selective cleavage

Model compound 3: For site selective cleavage

Model compound 1: For no site specific cleavage

Model compound 2: For site selective cleavage

Model compound 3: For site selective cleavage

Concentration: 16μM — Nicked DNA / Supercoiled DNA
Concentration: 100μM — Nicked DNA / Supercoiled DNA
Concentration: 40μM — Nicked DNA / Supercoiled DNA
Concentration: 250μM — Nicked DNA / Supercoiled DNA (R,R)-11

(S,S)-11

POLYNUCLEOTIDE CLEAVAGE AGENT SWITCHED ON BY PHOTO IRRADIATION

TECHNICAL FIELD

The present invention relates to a polynucleotide cleavage agent switched on by photo-irradiation and a method of cleaving or decomposing polynucleotide such as DNA or RNA using the polynucleotide cleavage agent switched on by the photo-irradiation.

BACKGROUND OF THE INVENTION

Natural restriction enzymes are now essential for gene engineering and many types of restriction enzymes from microbes, plants, or animals are commercially available. Various kinds of these enzymes are known, for example, EcoR I which is isolated from *Escherichia coli*. They are very expensive, must be handled under conditions of low temperature and require storage in a refrigerator or freezer at below −20° C. In addition, it is impossible to design the cleaving point artificially because they are natural proteins.

So called "tailor-made" polynucleotide cleavage agents which can cleave DNA or RNA selectively at a desired position, and which can be stored at room temperature are therefore required.

Many types of natural DNA cleavage agents are known to work as strong anti-tumor or anti-cancer medicines. Among them, calicheamicin is a well respected potent anti-tumor medication. The origin of its DNA cleavage activity has been proposed as being from a biradical intermediate that is produced by the degradation process from an unstable ene-diyne group to a stable aromatic ring.

Extensive studies have been made to develop an artificial restriction enzyme which can cleave a DNA sequence selectively. Recently, simple anthracene or anthraquinone derivatives have been reported as potent DNA cleavage agents: Schuster and co-workers reported that AQC caused GG selective cleavage of duplex DNA (*J. Am. Chem. Soc.* 1996, 118, 8747), and Kumar succeeded in cleaving DNA by simple anthracene derivatives (*Tetrahedron*, 2000, 56, 7027). Toshima developed a novel quinoxaline-carbohydrate hybrid as a GG-selective DNA cleaving agent with DNA cleavage and binding abilities which are dependent on the structure of the sugar moiety (Angew. Chem., Int. Ed. Engl. 1997, 36, 2748; *Bioorganic & Medicinal Chem. Lett.* 2000, 10, 2163; *Chem. Commun.*, 212 (2002)). Artificial restriction enzymes by photo-irradiation which can be practically used have not been reported.

During the course of the study on the synthesis of optically active gem-difluoro-cyclopropane derivatives, we noted an interesting fact: the preparation of 9-anthracenecarboxylic acid ester of 1,3-bishydroxymethyl-2,2-difluoro-cyclopropane has to be performed under darkened conditions. Also, some papers on gem-difluoro-cyclopropane ring disclosed that an unidentified ring opening product was formed instead of the desired diester when the reaction was carried out under visible light irradiation conditions (*Chem. Lett.* 1998, 903; *Tetrahedron Lett.* 1999, 40, 5739), and a gem-difluoro-cyclopropane ring was easily decomposed and caused a ring opening reaction via a radical intermediate (Dolbier, Jr. et al., *J. Org. Chem.* 1999, 64, 540).

These findings stimulated to investigate the possibility of gem-difluoro-cyclopropane derivatives of 9-anthracene carboxylic acid as novel DNA cleavage agents. It was anticipated that strong DNA cleavage activity could be obtained by the synergetic effect of the difluoro-cyclopropane group with the anthracene carboxylic group. However, it was confirmed that there was no significant DNA cleavage activity for such 9-anthracene carboxylic diester of 1,3-bishydroxymethyl-2,2-difluoro-cyclopropane (The 25$^{th}$ Japanese Symposium on Fluorine Chemistry, Nov. 18, 2001, p. 54–55). Extensive studies have been made to develop strong DNA cleavage agents that can cleave a DNA sequence selectively when switched on by photo-irradiation and such compounds could serve as an anti-tumor medication.

SUMMARY OF THE INVENTION

The subject invention firstly provides a polynucleotide cleavage agent switched on by photo-irradiation which comprises cyclopropane or 2,2-dihalgeno-cyclopropane ring between "A" unit and "B" unit, wherein said "A" unit is an aromatic group having electron withdrawing property and is excited by photo-irradiation, and said "B" unit is a hydrophilic functional group (cf. FIG. 1, Model compounds 1 to 3).

Secondly, the present invention provides a polynucleotide cleavage agent switched on by photo-irradiation comprises cyclopropane or 2,2-halogeno-cyclopropane ring between "A" unit and "B" unit, and also a "C" unit, wherein said "A" unit and said "B" unit are as defined above and said "C" unit can recognize polynucleotides such as DNA sequences.

The agents can cleave DNA at a desired position by introduction of the "C" unit which recognizes a DNA sequence as shown in FIG. 1 (model 2 and model 3). A typical example of the "C" unit is an amino sugar, which may be connected with the 2,2-difluoro-cyclopropopane part using a spacer as shown in FIG. 1 (model 2).

Thirdly, the present invention provides a method of cleaving or decomposing a polynucleotide which comprises contacting said polynucleotide with the polynucleotide cleavage agent described above and then photo-irradiating to cleave said polynucleotide.

DETAILED DESCRIPTION OF THE PREFERRED EMBODIMENT

The wording "switched on by photo-irradiation" means that the cleavage activity is developed by photo-irradiation.

The term "halogeno" includes fluoro, chloro and bromo, with fluoro being preferred.

The term "polynucleotide" as used herein may include DNA, RNA, and the like and the term "DNA" is sometimes used here instead of "polynucleotide".

"A" unit of the invention comprises an aromatic group such as anthracene, pyren, fluorene, naphthalimide, quinoline, quinoxaline, anthraquinone, flavin, and the like, with anthracene, pyren and fluorene being preferred.

The aromatic group includes preferably an aryl carbonyl group such as anthracene-, pyren-, fluorene-, naphthalimide-, quinoline-, quinoxaline-, anthraquinone- and flavin-carboxylic moiety, with anthracene-, pyren- and fluorene-carboxylic moiety being preferred.

"B" unit of the invention is a hydrophilic functional group, and hydrophilicity of this unit may strengthen the binding property with DNA, allowing the cyclopropane group to interact with the DNA easily. "B" unit is also the preferably positively charged group which may bind with a phosphate group in DNA, such as amino-, alkylamino-, carbamoyl, hydroxyl, ammonium group, and the like.

The preferred polynucleotide cleavage agents of the invention are those wherein said "A" unit is an arylcarboxylic moiety selected from a group consisting of anthracene-, pyren-, fluorene-, naphthalimide, quinoline, quinoxaline, anthraquinone and flavin-carboxylic moieties and, said "B" unit is a hydrophilic functional group selected from a group consisting of amino-, alkylamino-, carbamoyl, hydroxyl and ammonium groups.

3-Aminomethyl-2,2-difluoro-cyclopropylmethyl arylcarboxylate, 3-aminomethyl-cyclopropylmethyl arylcarboxylate, 3-aminomethyl-2,2-difluorocyclopropylmethyl arylcarboxamide and 3-aminomethylcyclopropylmethyl arylcarboxamide can be mentioned as preferred polynucleotide cleavage agents.

Specific preferable polynucleotide cleavage agents may be 3-aminomethyl-2,2-difluoro-cyclopropylmethyl 9-anthracene-carboxylate, 3-aminomethyl-2,2-difluoro-cyclopropylmethyl 9-anthracenecarboxamide, or 3-hydroxymethyl-2,2-difluoro-cyclopropylmethyl 9-anthracenecarboxamide, which are all novel compounds.

The polynucleotide cleavage agent of the present invention as defined above may also include "C" unit which can recognize DNA sequences. Examples of "C" unit include, but are not limited to, nucleic acids, peptide nucleotides, amino sugars with a spacer molecule, and the like. A peptide nucleotide may act as a polypeptide mimic, of which a nucleic acid moiety can recognize a desired site in a DNA sequence; therefore, such a peptide nucleotide may be a polynucleotide cleavage agent of the present invention with the faculty of "tailor made" restriction enzyme.

Figure 1:
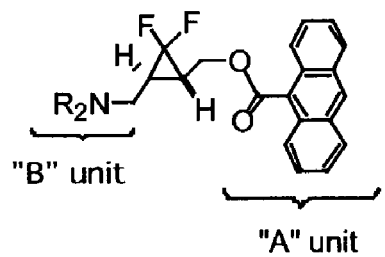
FIG. 1 shows model compounds 1 to 3 which are polynucleotide cleavage agents of the present invention.
Figure 1:
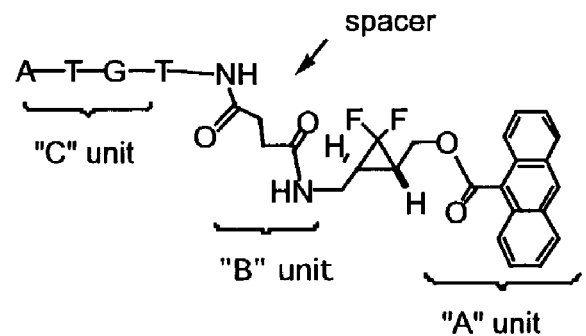
Figure 1:
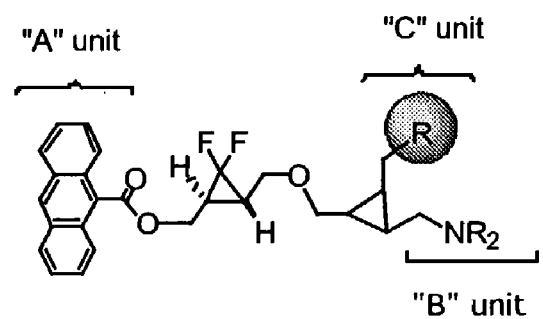

An amino group of a cyclopropane ring having the amino and a hydroxy group can bind to one carboxy group of succinic acid as a spacer molecule and the other carboxyl group can bind to a peptide nucleotide as a "C" unit (cf. FIG. 1, Model compound 2). Other simple functional groups can also be used as "C" unit if they can recognize a DNA sequence, because such recognition is the sole function requested of a member of the "C" unit.

Various types of compounds can be used as a spacer molecule if they can be connected both with a cyclopropyl group and a DNA recognizing functional group ("C" unit). Examples of spacer compounds include, but are not limited to, dicarboxylic acid, β-amino acids, diamide and the like.

The polynucleotide cleavage agent of the present invention as defined above may cleave or decompose at any random site(s) or at a desired site in a polynucleotide.

All stereo isomers of polynucleotide cleavage agent of the present invention are contemplated. The stereo isomers for 9-anthracenecarboxamide include (R,R)-, (S,S)-, (S,R)-, (R,S)-products and racemates thereof. The activity is generally independent of the absolute configuration of the cyclopropane ring for 9-anthracene-carboxamide. However, (R,R)-3-aminomethyl-2,2-difluorocyclopropylmethyl 9-anthracenecaroboxylate showed five times stronger activity than the corresponding (S,S)-isomer.

The polynucleotide cleavage agent of the present invention as defined above may cleave RNA and also shows anti-retro virus activity.

EXAMPLES

Example 1

Synthesis of (S,S)-3-aminomethyl-2,2-difluoro-cyclopropylmethyl anthracene-9-carboxylate((S,S)—NH$_2$-mono)

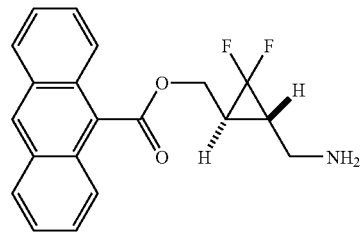

(S,S)-NH$_2$-mono

Scheme 1

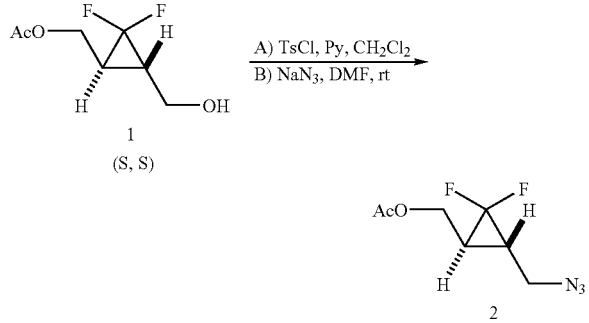

Part A. To a solution of monoacetate (S,S)-1 (3.37 g, 18.7 mmol) and p-toluenesulfonyl chloride (p-TsCl, 4.27 g, 22.4 mmol) in CH$_2$Cl$_2$ (50 mL) was added pyridine (2.27 mL, 28.1 mmol) at 0° C., and the mixture was stirred at rt for 29 h. The reaction was quenched with water (20 mL) and extracted with CH$_2$Cl$_2$ (50 mL) and ethyl acetate (20 mL, 3 times). The combined organic layers were dried over MgSO$_4$ and concentrated; Purification by silica gel flash column chromatography (hexane/ethyl acetate=10:1 to 4:1) then gave the tosylate (4.20 g, 12.04 mmol) in 64% yield. (Itoh, T.; Ishida, N.; Mitsukura, K.; Uneyama, K. J. *Fluorine Chem.* 2001, 112, 63–68).

Part B. To a solution of 3-(p-toluene)sulfonyloxy-methyl-2-difluorocyclopropylmethyl acetate (100.3 mg, 0.30 mmol) in N,N-dimethylformamide (DMF, 1.5 mL) was added sodium azide powder (29.3 mg, 0.45 mmol) in a single portion under argon and the mixture was stirred at rt for 11 h, then quenched with crushed ice and extracted with ether (5 mL, 4 times). The combined organic layers were dried over MgSO$_4$, concentrated, and purification by silica gel thin layer chromatography (hexane/ethyl acetate=2:1) gave azide 2 (59.6 mg, 0.29 mmol) in 97% yield.

R$_f$ 0.50 (hexane/ethyl acetate=4:1); $^1$H NMR (200 MHz, δ, CDCl$_3$, J=Hz) 1.58–1.98 (2H, m), 2.08 (3H, s), 3.36 (2H, ddd, J=26.8, 13.7, 7.3), 4.01–4.28 (2H, m); $^{13}$C NMR (50 MHz, ppm, CDCl$_3$, J=Hz) 20.59, 25.95 (t, J$_{C-F}$=10.7), 26.49 (t, J$_{C-F}$=10.7), 47.73 (d, J$_{C-F}$=3.6), 60.29 (d, J$_{C-F}$=4.1), 113.00 (t, J$_{C-F}$=285.6), 170.68; $^{19}$F NMR (188 MHz, ppm, CDCl$_3$, J=Hz) 23.22 (1F, dd, J$_{F-F}$=165.0, J$_{F-F}$=11. 4), 24.41 (1F, dd, J$_{F-F}$=165.0, J$_{H-F}$=11.7); IR (neat, cm$^{-1}$) 2957, 2099, 1743, 1481, 1369, 1235, 1140, 1018, 890, 758.

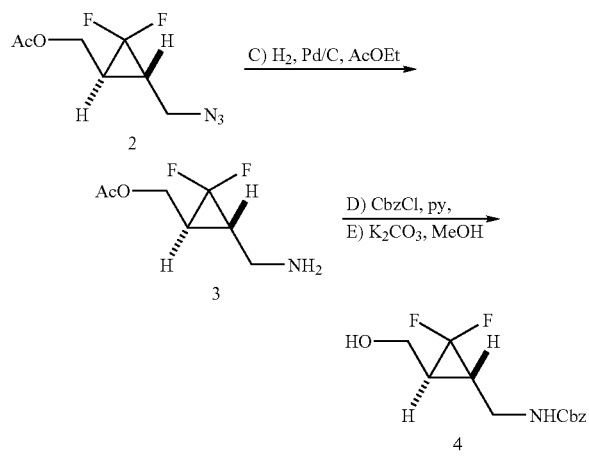

Scheme 2

Part C. A solution of azide 2 (27 mg, 0.132 mmol) in ethyl acetate (1.5 mL) and methanol (0.5 mL) was stirred at rt in the presence of Pd/C (5.4 mg, 20 wt %) under H$_2$ (1 atm) for 3 h. The crude product was filetred through a sintered glass filter with a Celite pad, and the filtrate was concentrated to afford amine 3 (21.8 mg, 0.12 mmol) as a yellow oil in 93% yield.

R$_f$ 0.26 (dichloromethane/methanol=3:1); $^1$H NMR (200 MHz, δ, CDCl$_3$, J=Hz) 1.50–1.83 (2H, m), 1.90 (2H, br s), 2.06 (3H, s), 2.70–2.95 (2H, m), 3.95–4.25 (2H, m);

19F NMR (188 MHz, ppm, CDCl$_3$, J=Hz) 21.75 (1F, dd, J$_{F-F}$=163.4, J$_{H-F}$=13.2), 24.26 (1F, dd, J$_{F-F}$=163.5, J$_{H-F}$=13.7); IR (neat, cm$^{-1}$) 3367, 2944, 1379, 1659, 1564, 1480, 1370, 1238, 1035, 719, 607.

Part D. To a solution of 3 (35 mg, 0.195 mmol) and benzyloxycarbonyl chloride (CbzCl, 50 mg, 0.29 mmol) in dioxane (1 mL) was added pyridine (31 mg, 0.39 mmol) at rt and the mixture was stirred at 55° C. for 4 h. After being allowed to cool to rt, the reaction mixture was diluted with ethyl acetate (5 mL) and brine (5 mL) and was extracted with ethyl acetate (5 mL, 3 time). The combined organic layers were dried over MgSO$_{41}$ concentrated, and the crude product was purified by silica gel TLC (hexane/ethyl acetate=5:1, twice) to give N-Cbz-protected compound (47.3 mg, 0.15 mmol) in 77% yield.

R$_f$ 0.54 (hexane/ethyl acetate=2:1); $^1$H NMR (200 MHz, δ, CDCl$_3$, J=Hz) 1.66–1.92 (2H, m), 2.05 (3H, s), 3.10–3.33 (1H, m), 3.37–3.62 (1H, m), 3.95–4.23 (2H, m), 5.00 (1H, br s), 5.12 (2H, s), 7.30–7.45 (5H, m); $^{13}$C NMR (50 MHz, ppm, CDCl$_3$, J=Hz) 20.72, 25.92 (t, J$_{C-F}$=10.8), 26.95 (t, J$_{C-F}$=10.2), 38.23 (d, J$_{C-F}$=3.7), 60.70 (d, J$_{C-F}$=4.3), 66.93, 114.51 (t, J$_{C-F}$=287.1), 136.17, 156.23, 170.86; $^{19}$F NMR (188 MHz, ppm, CDCl$_3$, J=Hz) 22.38 (1F, dd, J$_{F-F}$=164.0, J$_{H-F}$=11.4), 23.62 (1F, dd, J$_{F-F}$=164.5, J$_{H-F}$=11.2); IR (neat, cm$^{-1}$) 3343, 3033, 2956, 1703, 1526, 1479, 1368, 1234, 1145, 1038, 749, 699.

Part E. To a solution of N-Cbz-protected compound (12.8 mg, 0.0409 mmol) in methanol (0.2 mL) was added K$_2$CO$_3$ (6.7 mg, 0.482 mmol) at rt and this was stirred for 5.5 h at the same temperature. Several pieces of crushed ice and NaCl (0.5 g) were added to the mixture, and the resulting mixture was extracted with ethyl acetate (5 mL, 4 times). The combined organic layers were dried over MgSO$_4$ and concentrated under a reduced pressure. Aminoalcohol 4 (9.8 mg, 0.036 mmol) was isolated by silica gel TLC (hexane/ethyl acetate=2:1, 2 times) in 88% yield.

R$_f$ 0.29 (hexane/ethyl acetate=2:1); $^1$H NMR (200 MHz, δ, CDCl$_3$, J=Hz) 1.48–1.91 (2H, m), 3.06–3.29 (1H, m), 3.29–3.50 (1H, m), 3.50–3.81 (2H, m), 4.96 (1H, br s), 5.04 (2H, s), 7.21–7.40 (5H, m); $^{13}$C NMR (50 MHz, ppm, CDCl$_3$, J=Hz) 26.63 (t, J$_{C-F}$=10.3), 29.42 (t, J$_{C-F}$=10.1), 38.19, 59.10, 67.03, 112.17 (t, J$_{C-F}$=286.8), 128.95, 129.07, 129.37, 136.18, 157.41; $^{19}$F NMR (188 MHz, ppm, CDCl$_3$, J=Hz) 23.26 (2F, d, J$_{H-F}$=9.4); IR (neat, cm$^{-1}$) 3330, 3034, 2955, 1698, 1536, 1478, 1257, 1182, 1131, 1007, 740, 698.

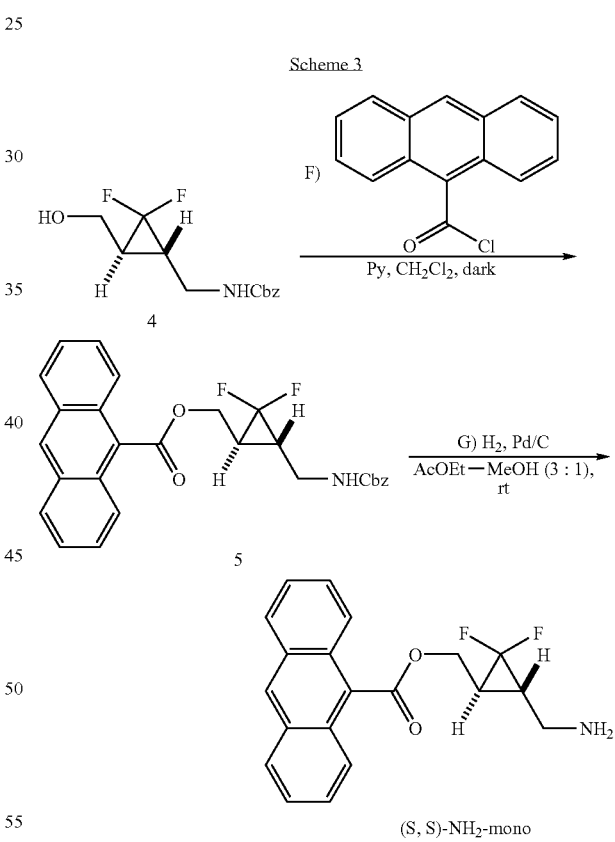

Scheme 3

Part F. To a solution of oxalyl chloride (234 mg, 1.84 mmol) in benzene (1 mL) was added 9-anthracene-carboxylic acid (37.6 mg, 0.168 mmol) at rt, the mixture was heated under reflux conditions for 9 h, allowed to cool to rt, and the solvent was removed under reduced pressure to give a residue. This residue was diluted with CH$_2$Cl$_2$ (0.5 mL), then to the resulting solution, pyridine (60.2 mg, 0.762 mmol) was added at 0° C. under dark conditions, and the mixture was stirred for 20 min at rt. A solution of 4 (41.0 mg, 0.152 mmol) in CH$_2$Cl$_2$ (0.5 mL) was added at 0° C. under argon and the mixture was allowed to cool to rt with vigorous stirring for 3 h in a dark place. The reaction mixture was quenched with crushed ice and diluted with ethyl acetate (10 mL) and brine (10 mL); the resulting mixture was extracted with ethyl acetate (5 mL, 3 times). The combined organic layers were dried over $MgSO_4$ and concentrated, and finally, silica gel flash column chromatography (hexane/ethyl acetate=10:1 to 2:1) gave ester 5 (24.3 mg, 0.0511 mmol) in 31% yield.

$R_f$ 0.54 (hexane/ethyl acetate=2:1); $^1$H NMR (200 MHz, δ, $CDCl_3$, J=Hz) 1.85–2.22 (2H, m), 3.14–3.36 (1H, m), 3.47–3.74 (1H, m), 4.50–4.81 (2H, m), 4.95 (1H, br s), 5.02 (2H, s), 7.19–7.40 (5H, m), 7.40–7.65 (4H, m), 8.04 (4H, d, J=8.4), 8.55 (1H, s); $^{19}$F NMR (188 MHz, ppm, $CDCl_3$, J=Hz) 22.14 (IF, dd, $J_{F-F}$=165.5, $J_{H-F}$=11.9), 23.76 (1F, dd, $J_{H-F}$=164.8, $J_{H-F}$=12.2); IR (neat, $cm^{-1}$) 3355, 3058, 2957, 1718, 1523, 1477, 1200, 1148, 1102, 894, 734, 698.

Part G. A solution of ester 5 (14.6 mg, 0.0307 mmol) in methanol (0.3 mL) was stirred at rt in the presence of Pd/C (3.0 mg, 20 wt %) under $H_2$ (1 atm) for 15 h in the dark. The crude products were filtered through a sintered glass filter with a Celite pad, and the filtrate was dried under vacuo to afford the title compound (S,S)—$NH_2$-mono(9.2 mg, 0.027 mmol) in 88% yield. This compound was unstable when dissolved in methanol or $CHCl_3$ under the irradiation of sunlight; therefore, it should be kept under an argon atmosphere in a dark place.

(S, S)—$NH_2$-mono:

$R_f$ 0.1 (Hexane/ethyl acetate=1:3); $[\alpha]^{21}{}_D$305.40 (c1.0, MeOH); $^1$H NMR (270 MHz, ppm, $CDCl_3$, J=Hz) 2.13–2.15 (2H, m), 4.50–4.89 (4H, m), 7.58–7.68 (4H, m), 7.39–8.09 (4H, m) 8.53 (1H, s); $^{13}$C NMR (125.8 MHz, ppm, $CDCl_3$, J=Hz) 24.79 (t, $J_{C-F}$=11.6), 26.88 (t, $J_{C-F}$=10.6), 37.28, 62.32, 114.00 (t, $J_{C-F}$=285.5), 126.27, 129.42, 129.51, 129.61, 132.63, 132.71, 133.37, 170.24; $^{19}$F NMR (470.6 MHz, ppm, $CDCl_3$, J=Hz) 23.50 (2F, s); IR (neat, $cm^{-1}$) 3348, 2941, 2829, 1732, 1605, 1474, 1261, 1205, 1154

Example 2

DNA cleavage test using (S,S)—$NH_2$-mono under photoirradiation φX174 RFI DNA (New England BioLabs, N3021S, 150 [M] (1 [L]) was dissolved in a 10 mM sodium phosphate buffer pH 7.0 (9 [L]) in a micro tube.

Ethyl 9-anthracene carboxylate (anth-OEt) was used as a control compound. Three samples were prepared: a buffer solution of DNA, a mixture of anth-OEt with a buffer solution of DNA, and a mixture of (S,S)—$NH_2$-mono with a buffer solution of DNA. These samples were placed under a UV-A lamp (max=365 nm, trans illuminator) at a distance of 4 cm, and irradiated for 3 h. The resulting mixture was subjected to an electrophoresis experiment (8% agarose gel, TAE buffer, 100 V, 30 min). The resulting agarose gel was stained with ethidium bromide (EtBr), visualized by UV-B lamp and the DNA cleavage ratio was determined by NIH Image 1.62.

Experimental conditions of ø4X174 RFI DNA

| Entry | DNA | Sample | Buffer solution |
|---|---|---|---|
| 1 | 1 [L | DMSO, 1 [L | 9 [L |
| 2 | 1 [L | $NH_2$-mono 1 mM, 1 [L | 9 [L |
| 3 | 1 [L | $NH_2$-mono 5 mM, 1 [L | 9 [L |
| 4 | 1 [L | $NH_2$-mono 12 mM, 1 [L | 9 [L |

-continued

Experimental conditions of ø4X174 RFI DNA

| Entry | DNA | Sample | Buffer solution |
|---|---|---|---|
| 5 | 1 [L | anth-OEt 1 mM, 1 [L | 9 [L |
| 6 | 1 [L | anth-OEt 5 mM, 1 [L | 9 [L |
| 7 | 1 [L | anth-OEt 12 mM, 1 [L | 9 [L |
| 8 | 1 [L | DMSO, 1 [L | 9 [L |

Buffer solution: 10 mM sodium phosphate pH 7.0

Figure 2:
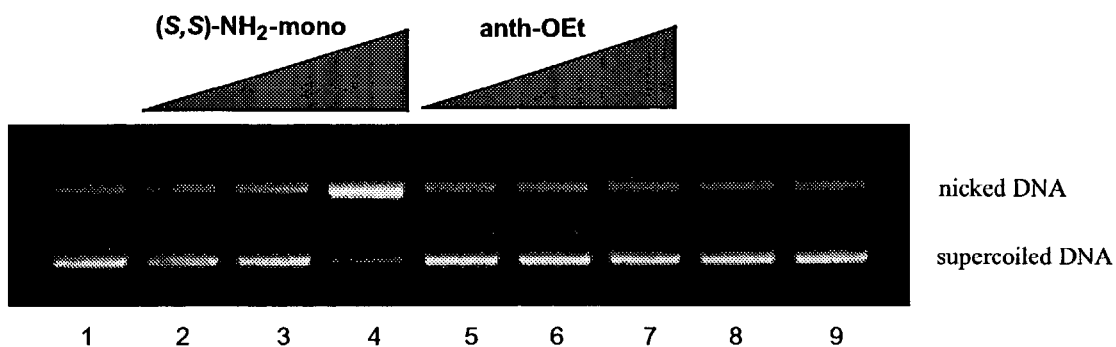
FIG. 2 shows a chart of electrophoresis after photocleavage of supercoiled φX174 plasmid DNA by 9-anthracenecarboxylates (S,S)—NH$_2$-mono and anth-OEt.
Figure 3:
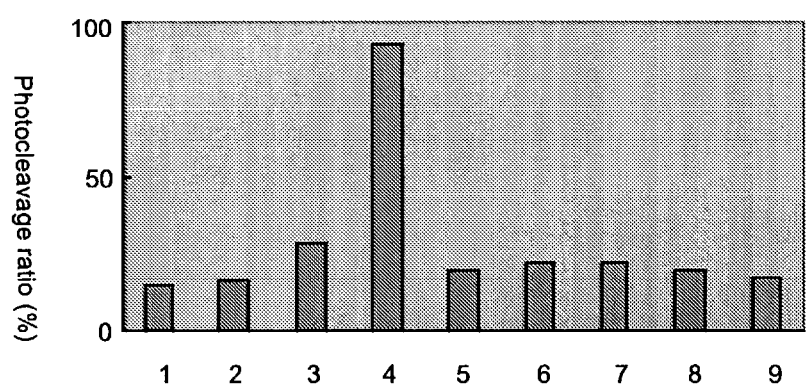
FIG. 3 shows a column graph which is quantitatively converted from the chart of electrophoresis after photocleavage of supercoiled φX174 plasmid DNA by 9-anthracenecarboxylates (S,S)—NH$_2$-mono and anth-OEt as shown in FIG. 2.

The results are shown in FIGS. 2 and 3. FIG. 2 shows a chart of electrophoresis after photocleavage of φX174 RFI DNA with 9-anthracenecarboxylates of (S,S)—$NH_2$-mono and anth-OEt. The increased ratio of nicked DNA means that DNA was cleaved by the experimental conditions. FIG. 3 shows a column graph which is quantitatively converted from the chart of electrophoresis as shown FIG. 2. A percentage shows the results of the DNA cleaved ratio under the experimental conditions.

Results (S,S)—$NH_2$-mono was found to cause cleavage of DNA and to work as a weak DNA cleavage agent, while 9-anthracene-carboxylic acid ethyl ester (anth-OEt) showed no significant activity. It was confirmed that no DNA cleavage took place under reaction conditions without (S,S)—$NH_2$-mono.

Discussions

This experiment shows that φX174 RFI DNA was cleaved without site selectivity. It is believed that site selective cleavage may be possible using properly modified compounds which have a functional group that interacts with DNA at a specific position.

3-Aminomethyl-2,2-difluorocyclopropylmethyl 9-anthracenecarobxylate may act as an anti-cancer medicine because it can cleave DNA.

Example 3

Synthesis of (R,R)-3-aminomethyl-2,2-difluoro-cyclopropylmethyl anthracene-9-carboxylate((R,R)—$NH_2$-mono)

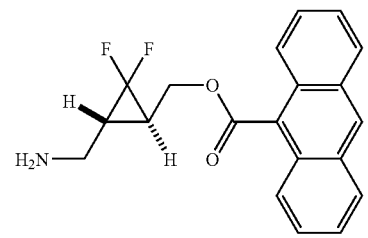

(R,R)-$NH_2$-mono

Starting from (R,R)-1,3-bishydroxymethyl-2,2-difluoro-cyclopropane, (R,R)—$NH_2$-mono was prepared by the same procedures as described in Example 1.

Example 4

Synthesis of (R,R)-3-aminomethyl-2,2-difluoro-cyclopropylmethyl anthracene-9-carboxylate((R,R)—$NH_2$-mono) (by an alternative method)

Scheme 4

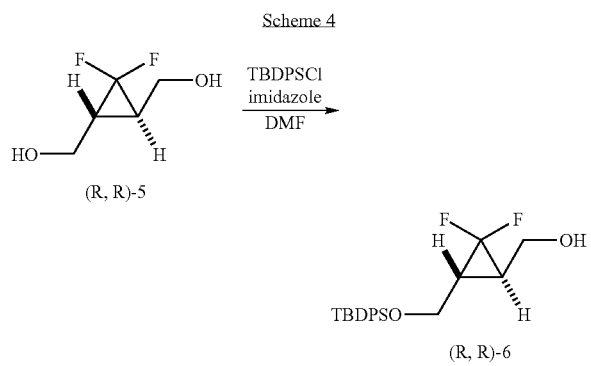

To a solution of (R,R)-1,3-bishydroxy-methyl-2,2-difluoro-cyclopropane ((R,R)-5)(414 mg, 3.00 mmol, 99% ee) and tert-butyldiphenyl-chlorosilan (TBDPSCl)(1.24 g, 4.50 mmol) in N,N-dimethylformamide (DMF)(15 mL) was added imidazole (306 mg, 4.50 mmol), and the mixture was stirred at rt for 24 h. The reaction was quenched with crushed ice and extracted with ether (10 ml, 4 times). The combined organic layers were dried over MgSO$_4$, concentrated, and silica gel flash column chromatography (hexane/ethyl acetate=50:1 to 4:1) gave (R,R)-6 (511 mg 1.36 mmol) in 45% yield. Bis-TBDPS ether was also obtained (821 mg 1.34 mmol) in 45% yield.

R$_f$ 0.30 (Hexane/ethyl acetate=2:1); bp 200° C./2.4 Torr (Kugelrohr); [α]$^{26}_D$+3.8 (c. 1.56, CHCl$_3$); $^1$H NMR (270 MHZ, ppm, CDCl$_3$, J=Hz) 1.04 (9H, S), 1.61–1.72 (2H, m), 3.64–3.79 (4H, m), 7.35–7.47 (6H, m), 7.64–7.67 (4H, m); $^{13}$C NMR (125.8 MHz, ppm, CDCl$_3$, J=Hz) 19.01, 26.71, 28.54 (t, J$_{C-F}$=10.1), 28.70 (t, J$_{C-F}$=10.1), 59.51 (d, J$_{C-F}$=4.8), 60.17 (d, J$_{C-F}$=3.9), 114.64 (t, J$_{C-F}$=286.5), 127.89, 129.96, 133.29, 133.39, 135.65; $^{19}$F NMR (470.6 MHz, ppm, CDCl$_3$, J=Hz) 23.06 (1F, dd, J$_{F-F}$=162.4, J$_{H-F}$=11.1), 23.63 (1F, dd, J$_{F-F}$=164.1, J$_{H-F}$=11.5); IR (neat, cm$^{-1}$) 3366, 2932, 2858, 1472, 1261, 1184, 1113, 1013, 702.

Scheme 5

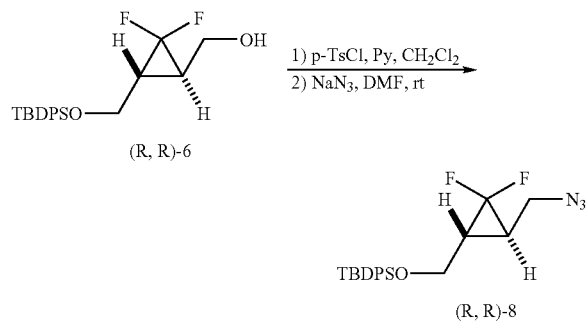

To a solution of (R,R)-6 (1.50 g, 3.98 mmol) and p-toluenesulfonyl chloride (p-TsCl) (2.28 g, 11.9 mmol) in dichloromethane (CH$_2$Cl$_2$) (20 mL) was added pyridine (1.50 mL, 17.9 mmol) at 0° C., and the mixture was stirred at rt for 24 h. The reaction was quenched with water (10 ml) and then extracted with CH$_2$Cl$_2$ and ethyl acetate (10 ml, 3 times). The combined organic layers were dried over MgSO$_4$ and silica gel flash column chromatography (hexane/ethyl acetate=300:1 to 4:1) gave the corresponding tosylate ((R,R)-7) (1.60 g, 3.01 mmol) in 76% yield. This was used without further purification. To a solution of the tosylate (400 mg, 0.75 mmol) in DMF (8 mL) was added sodium azide powder (73 mg, 1.13 mmol) in one portion and the mixture was stirred at rt for 10 h. The reaction was quenched with crushed ice and extracted with ether (10 ml, 4 times). The combined organic layers were dried over MgSO$_4$ and silica gel flash column chromatography (hexane/ethyl acetate=50:1 to 10:1) gave (R,R)-8 (289 mg, 0.72 mmol) in 96% yield.

bp 130° C./1.6 Torr (kugelrohr); [α]$^{22}_D$–14.1 (c. 1.47, CHCl$_3$); R$_f$ 0.70 (Hexane/ethyl acetate=7:1); $^1$H NMR (270 MHz, ppm, CDCl$_3$, J=Hz) 1.05 (9H, s), 1.55–1.74 (2H, m), 3.30 (2H, d, J$_{C-F}$=6.0), 3.73–3.79 (2H, m), 7.25–7.47 (6H, m), 7.64–7.67 (4H, m); $^{13}$C NMR (125.8 MHz, ppm, CDCl$_3$, J=Hz) 19.27, 25.22 (t, J$_{C-F}$=10.6), 28.86, 29.72 (t, J$_{C-F}$=10.1), 48.18 (d, J$_{C-F}$=4.8), 59.87 (d, J$_{C-F}$=5.0), 113.77 (dd, J$_{C-F}$=286.1288.9), 127.94, 130.02, 133.22, 133.31, 135.68; $^{19}$F NMR (470.6 MHz, ppm, CDCl$_3$, J=Hz) 22.82 (1F, dd, J$_{F-F}$=160.0, J$_{H-F}$=11.5), 24.74 (1F, dd, J$_{F-F}$=164.4, J$_{H-F}$=14.4); IR (neat, cm$^{-1}$) 2932, 2858, 2098, 1458, 1429, 1261, 1186, 1113, 1007, 834, 702.

Scheme 6

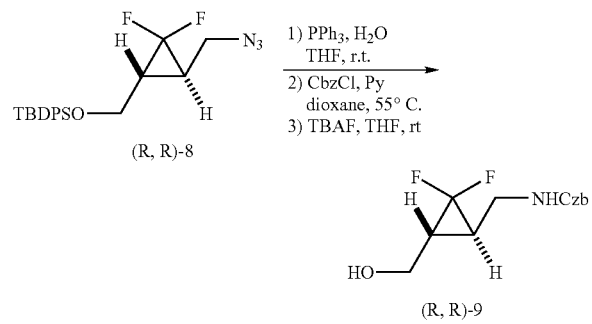

(R,R)-8 (494 mg, 1.23 mmol) and triphenylphosphine (354 mg, 1.35 mmol) was dissolved in a mixed solvent of THF and water (THF/H$_2$O=10 mL/40 mg) (10 mL), and the mixture was stirred at rt for 24 h and concentrated under vacuum. To the resulting residue was added a solution of benzyloxycarbonyl chloride (CbzCl, 420 mg, 2.46 mmol) and pyridine (0.3 mL, 3.69 mmol) in dioxane (10 mL) at rt, and the mixture was stirred at 55° C. for 12 h. After cooling to rt, ethyl acetate (15 mL) and brine (15 mL) were added and the mixture was extracted with ethyl acetate (15 mL, 4 times). The combined organic layers were dried over MgSO$_4$, concentrated, and silica gel flash column chromatography (hexane/ethyl acetate=50:1 to 4:1) gave the corresponding amide (533 mg 1.05 mmol) in 85% yield (2 steps). To a solution of the amide (300 mg, 0.589 mmol) in THF (5 mL) was added a solution of TBAF (0.89 mL, 0.89 mmol) in THF at rt and the mixture was stirred for 20 h. The reaction mixture was diluted with ethyl acetate. The organic layers were concentrated and subsequent silica gel flash column chromatography (hexane/ethyl acetate=10:1 to 0:1) gave (R,R)-9 (160 mg 0.589 mmol) in quantitative yield.

R$_f$ 0.20 (Hexane/ethyl acetate=2:1); bp 140° C./3.2 Torr (Kugelrohr); $^1$H NMR (270 MHz, ppm, CDCl$_3$, J=Hz) 2.10 (2H, m), 3.18–3.71 (4H, m), 5.03 (2H, s), 7.28 (5H, s); $^{13}$C NMR (125.8 MHz, ppm, CDCl$_3$, J=Hz) 26.41 (t, J$_{C-F}$=9.6), 29.01 (t, J$_{C-F}$=9.6), 37.94, 58.54, 66.81, 114.32 (t, J$_{C-F}$=278.0), 127.51, 127.95, 128.12, 136.10, 156.64; $^{19}$F NMR (470.6 MHz, ppm, CDCl$_3$, J=Hz) 23.46 (2F, s); IR (neat, cm$^{-1}$) 3325, 2923, 1699, 1456, 1182, 1130, 1042, 1005.

Scheme 7

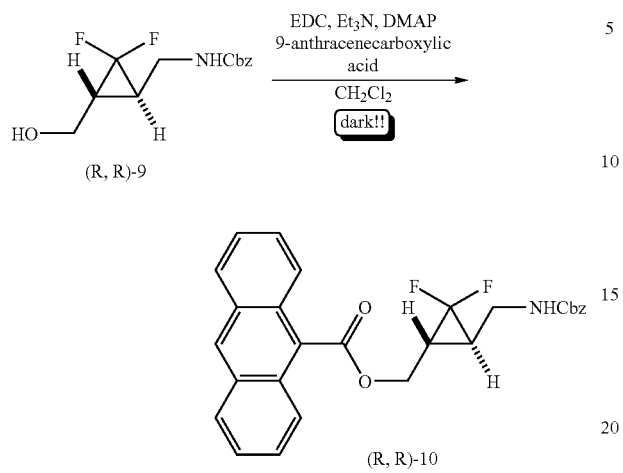

The reaction was carried out in a flask that was covered with aluminum foil to keep out light. To a CH₂Cl₂ (5 mL) solution of (R,R)-9 (65 mg, 0.240 mmol) was added EDC (75 mg, 0.390 mmol), 9-anthracenecarboxylic acid (59 mg, 0.264 mmol), and DMAP (8 mg, 0.072 mmol) at rt, then Et₃N (0.05 mL, 0.390 mmol) was added to the mixture at 0° C. and it was stirred for 4 h at 60° C. in a dark place. After being cooled to rt, the reaction mixture was diluted with ethyl acetate (6 mL) and extracted with ethyl acetate 6 times (10 mL each time). The combined organic layers were washed with NaHCO₃ and brine and dried over MgSO₄. Silica gel TLC (hexane/ethyl acetate=2:1) gave (R,R)-10 (20 mg, 0.042 mmol) in 18% yield, while the starting (R,R)-9 (42 mg, 0.156 mmol) was recovered in 65% yield.

$R_f$ 0.60 (Hexane/ethyl acetate=2:1); ¹H NMR (270 MHz, ppm, CDCl₃, J=Hz) 1.88–2.04 (2H, m), 3.12–3.23 (1H, m), 3.49–3.56 (1H, m), 4.48–4.63 (2H, m) 4.94 (2H, s), 7.20–7.27 (5H, m), 7.38–7.51 (4H, m) 7.93–7.98 (4H, m), 8.46 (1H, s); ¹³C NMR (125.8 MHz, ppm, CDCl₃, J=Hz) 25.82 (t, $J_{C-F}$=10.6), 27.28 (t, $J_{C-F}$=10.1), 38.12, 61.72, 66.91, 113.77 (t, $J_{C-F}$=287.5), 124.72, 125.51, 126.86, 127.12, 127.73, 128.08, 128.18, 128.50, 128.65, 129.75, 130.89, 136.10, 156.19, 169.30; ¹⁹F NMR (470.6 MHz, ppm, CDCl₃, J=Hz) 22.23 (1F, dd, $J_{F-F}$=166.9, $J_{H-F}$=14.4), 23.64 (1F, dd, $J_{F-F}$=165.6, $J_{H-F}$=13.0); IR (neat, cm⁻¹) 3342, 3064, 3034, 2964, 1717, 1456, 1201, 1173, 1003, 733.

Scheme 8

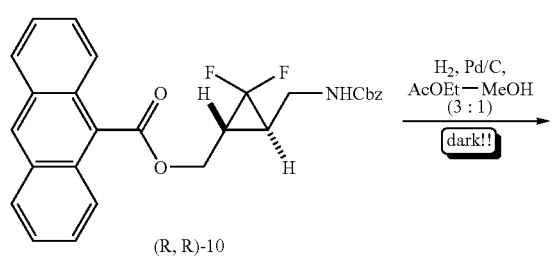

The reaction was carried out in a flask that was covered by aluminum foil to keep out light. A solution of (R,R)-10 (18 mg, 0.038 mmol) in methanol (1.0 mL) was stirred at rt in the presence of Pd/C (5.4 mg, 30 wt %) under H₂ (1 atom) for 5 days and filtered though a glass sintered glass filter with a Celite pad. The filtrate was evaporated under reduced pressure to give (R,R)—NH₂-mono (9.9 mg, 0.042 mmol). This compound was unstable when dissolved in methanol or CHCl₃ under the irradiation of sunlight; therefore, it should be kept under an argon atmosphere in a dark place.

(R,R)—NH₂-mono:

$R_f$ 0.1 (Hexane/ethyl acetate=1:3); $[\alpha]^{21}_D$ –5.60 (c2.0, MeOH); ¹H NMR (270 MHz, ppm, CDCl₃, J=Hz) 2.13–2.15 (2H, m), 4.50–4.89 (4H, m), 7.58–7.68 (4H, m), 7.39–8.09 (4H, m) 8.53 (1H, s); ¹³C NMR (125.8 MHz, ppm, CDCl₃, J=Hz) 24.79 (t, $J_{C-F}$=11.6), 26.88 (t, $J_{C-F}$=10.6), 37.28, 62.32, 114.00 (t, $J_{C-F}$=285.5), 126.27, 129.42, 129.51, 129.61, 132.63, 132.71, 133.37, 170.24; ¹⁹F NMR (470.6 MHz, ppm, CDCl₃, J=Hz) 23.50 (2F, s); IR (neat, cm⁻¹) 3348, 2941, 2829, 1732, 1605, 1474, 1261, 1205, 1153, 1024

Example 5

Figure 4:
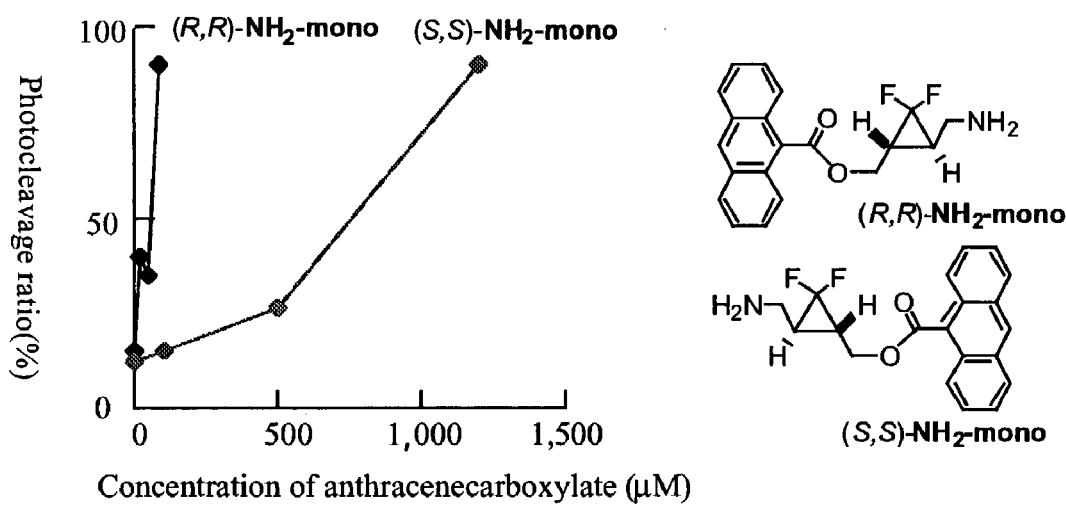
FIG. 4 shows a line graph of photocleavage of supercoiled φX174 plasmid DNA by 9-anthracenecarboxylates (S,S)-NH$_2$-mono and (R,R)—NH$_2$-mono.

DNA cleavage test using (R,R)— and (S,S)—NH₂-mono under photo-irradiation (FIG. 4)

The test was carried out using (R,R)— and (S,S)—NH₂-mono in the same manner as described in Example 2 except that the test samples were placed under a Xe lamp with a polystylene filter at a distance of 3 cm and irradiated for 2 hrs.

Results and Discussion

As expected, remarkable DNA cleavage was observed for 9-anthracenecarbonyl substituted cyclopropane derivatives as shown in FIG. 4.

Although (R,R)—NH₂-mono and (S,S)—NH₂-mono were unstable after deprotection of the amino protecting group, the DNA cleavage test gave very interesting results. Clear contrast of the reactivity was found for both compounds. This test showed that 85.5 [M was required, which corresponded to 0.667 equivalent versus supercoiled φX-174 DNA, to convert the DNA to the corresponding nicked type DNA when (R,R)—NH₂-mono was tested: in contrast, 1200 [M was needed to realize the same activity for the (S,S)—NH₂-mono, and (R,R)—NH₂-mono was more than 10 times stronger than the (S,S)-isomer.

Example 6

Synthesis of (R,R)-2,2-difluoro-3-hydroxymethyl-cyclopropylmethyl anthracene-9-carboxamide ((R,R)-11)

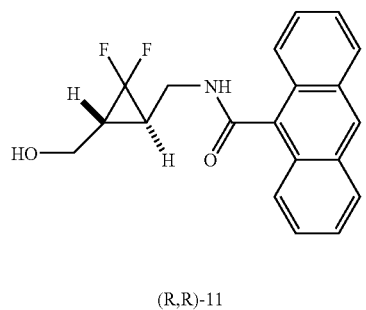

(R,R)-11

Scheme 9

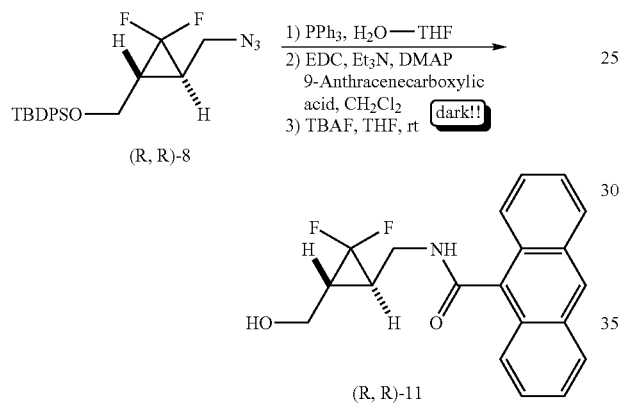

The reaction was carried out in a flask covered with aluminum foil to keep out the light. (R,R)-8 (100 mg, 0.249 mmol) and triphenylphosphine (72 mg, 0.27 mmol) were dissolved in a mixed solvent of tetrahydrofuran (THF) and water (THF/H$_2$O=10 mL/40 mg) (5 mL) and the mixture was stirred at rt for 24 h under an argon atmosphere, then solvent was removed under a vacuum. The resulting residue was diluted with CH$_2$Cl$_2$ (5 mL) and EDC (143 mg, 0.75 mmol), DMAP (3 mg, 0.02 mmol) and 9-anthracenecarboxylic acid (166 mg, 0.747 mmol) were added, then triethylamine (Et$_3$N) (0.1 mL, 0.747 mmol) was added at 0° C. The mixture was then stirred for 4 h at 60° C., cooled to rt, and diluted with ethyl acetate (60 mL). The organic layers ware washed with NaHCO$_3$ and brine, dried over MgSO$_4$, and evaporated under reduced pressure to give the corresponding amide (51 mg, 0.088 mmol) after silica gel thin layer chromatography (TLC) (hexane/ethyl acetate=2:1) in 35% yield. This was used for the next reaction without further purification.

To a THF (1.0 mL) solution of the amide (40 mg, 0.069 mmol) was added a 1.0 M THF solution of tetrabutylammonium fluoride (TBAF) (0.1 mL, 0.103 mmol) at rt and the mixture was stirred at rt for 6 h. A water and ethyl acetate was added which was extracted with ethyl acetate (5 mL, 4 times). The combined organic layers were dried over MgSO$_4$ and purified by silica gel TLC (hexane/ethyl acetate=1:3) to give (R,R)-11 (23 mg, 0.067 mmol) in 98% yield.

R$_f$ 0.35 (hexane/ethyl acetate=1:3); mp 186–193° C. (recrystallized from hexane-ether); $[\alpha]^{27}_D$+7.95 (c. 0.20, CHCl$_3$); $^1$H NMR (270 MHz, ppm, CDCl$_3$, J=Hz) 1.89–2.07 (2H, m), 3.67–3.77 (4H, m), 7.48–7.55 (4H, m), 8.05–8.08 (4H, m), 8.57 (1H, s); $^{13}$C NMR (125.8 MHz, ppm, CDCl$_3$, J=Hz) 26.57 (t, J$_{C-F}$=10.6), 30.23 (t, J$_{C-F}$=10.1), 37.37 (d, J$_{C-F}$=5.8), 58.70 (d, J$_{C-F}$=4.8), 115.64 (t, J$_{C-F}$=286.0), 125.35, 125.98, 127.12, 128.60, 128.64, 129.00, 131.95, 132.20, 171.81; $^{19}$F NMR (470.6 MHz, ppm, CDCl$_3$, J=Hz) 24.70 (2F, dd, J$_{F-F}$=364.2, J$_{H-F}$=15.8); IR (neat, cm$^{-1}$) 3260, 2926, 2855, 1628, 1549, 1248, 1178, 1115, 1003, 733.

Example 7

Synthesis of (S,S)-2,2-difluoro-3-hydroxymethyl-cyclopropylmethyl anthracene-9-carboxylic amide ((S,S)-11)

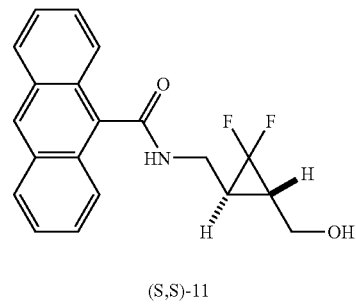

(S,S)-11

(S,S)-11 was prepared from (S,S)-8 corresponding to (R,R)-8 following the route described above.

$[\alpha]^{25}_D$–6.24 (c. 0.80, CHCl$_3$)

Example 8

Figure 5:
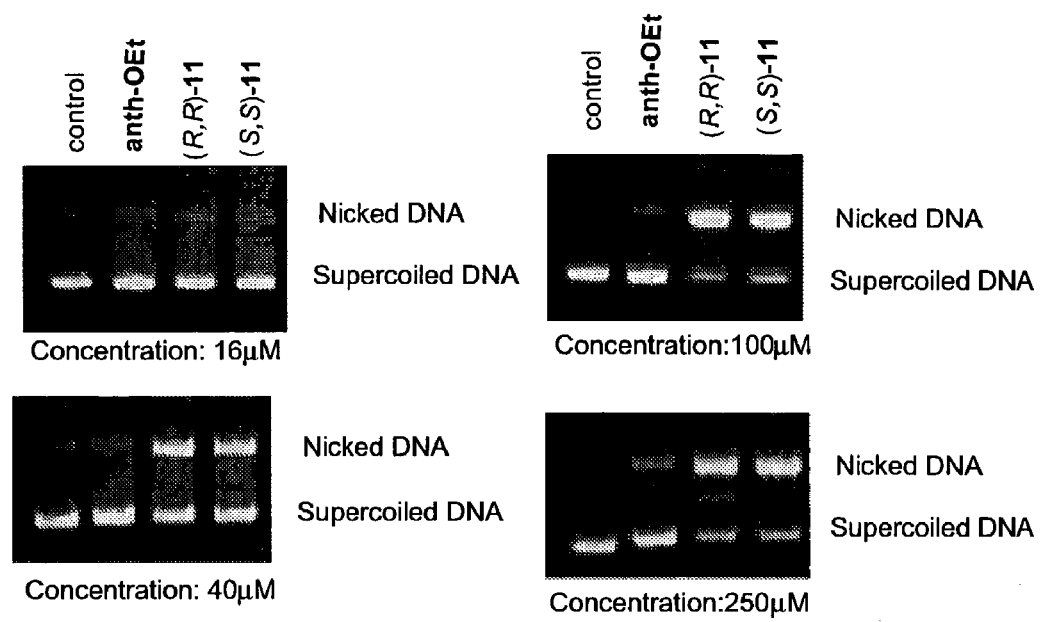
FIG. 5 shows a chart of electrophoresis after photocleavage of supercoiled φX174 plasmid DNA by anth-OEt, 9-anthracenecarboxamides (R,R)-11 and (S,S)-11.
Figure 5:
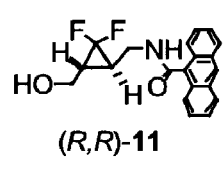
Figure 5:

DNA cleavage test using (R,R)- and (S,S)-11 (FIG. 5)

The reaction was carried out in a solvent of 20 mM sodium phosphate of pH 7.0 and 20% DMSO. Samples were irradiated for 45 min at a distance of 6 cm using Xe lamp using polystylene filter. Electrophoresis (0.8% agarose gel, TAE buffer, 100 V, 40 min). Gel was stained by EtBr and visualized by UV-B lamp (transillumnator).

Results and Discussion

The anthracenecarboxamide (R,R)-11, (S,S)-11 caused cleavage of DNA by photo-irradiation with a long wavelength UV light (365 nm): supercoiled φX174 DNA was converted to the nicked form in the presence of 100 µM of these compounds and this concentration corresponded to 1.3 equivalent versus the DNA base pair. As expected, there was strong DNA cleavage activity.

It has been established that anthracene carobonyl amide derivatives work as strong DNA cleavage agents switched on by photo-irradiation. However, (S,S)-11 showed the same activity as (R,R)-11 as shown in FIG. 5; it was found that the cleaving activity was independent of the absolute configuration of the difluoro-cyclopropane ring contradicting to the experiment using (R,R)— and (S,S)—NH$_2$-mono as DNA cleavage agents.

An artificial restriction enzyme is expected to be developed using the compounds of the present invention as base compounds. Such an understood enzyme should be useful not only for gene engineering but also for novel anti-cancer medicines. Since the compounds of the present invention are artificial, they have excellent flexibility for modification.

Proper modification of the compound may make it possible to cause DNA cleavage at the position desired.

In order to develop more efficient DNA cleavage active compounds based on proposed compounds, two strategies are suggested. The first is evaluation of the terminal "B" unit among various types of hydrophilic functional groups; increasing hydrophilicity of the "B" unit seems to strengthen its binding property with DNA, and allows the cyclopropane group to interact easily with the DNA. Electron positive hydrophilic groups are especially preferable as the "B" unit. The second is to design a molecule from the standpoint of stereochemistry. Since DNA consists of chiral sugars, the stereochemistry of the cyclopropane moiety may affect the DNA cleavage activity because of differences in the matching property with the sugar part of DNA or the helical pattern of the DNA sequence.

What is claimed is:

1. A polynucleotide cleavage agent switched on by photo-irradiation which comprises cyclopropane or 2,2-dihalogenocyclopropane ring between "A" unit and "B" unit, wherein said "A" unit is an aromatic group having electron withdrawing property and is excited by photo-irradiation, and said "B" unit is a hydrophilic functional group, wherein said aromatic group is an arylcarboxylic moiety.

2. The polynucleotide cleavage agent according to claim 1 which further comprises a spacer molecule.

3. The polynucleotide cleavage agent according to claim 1 wherein said 2,2-dihalogeno-cyclopropane is selected from a group consisting of 2,2-difluoro-, 2,2-dichloro- and 2,2-dibromo-cyclopropanes.

4. The polynucleotide cleavage agent according to claim 1 wherein said arylcarboxylic moiety is selected from a group consisting of anthracene-, pyren-, fluorene-, naphthalimide, quinoline, quinoxaline, anthraquinone and flavin-carboxylic moieties.

5. The polynucleotide cleavage agent according to claim 1 wherein said hydrophilic functional group is selected from a group consisting of amino-, alkylamino-, carbamoyl, hydroxyl and ammonium groups.

6. The polynucleotide cleavage agent according to claim 1 wherein said "A" unit is an arylcarboxylic moiety selected from a group consisting of anthracene-, pyren-, fluorene-, naphthalimide, quinoline, quinoxaline, anthraquinone and flavin-carboxylic moieties and, said "B" unit is a hydrophilic functional group selected from a group consisting of amino-, alkylamino-, carbamoyl, hydroxyl and ammonium groups.

7. The polynucleotide cleavage agent according to claim 1 which is selected from a group consisting of 3-aminomethyl-2,2-difluoro-cyclopropylmethyl arylcarboxylate, 3-aminomethyl-cyclopropylmethyl arylcarboxylate,3-aminomethyl-2,2-difluoro-cyclopropylmethyl arylcarboxamide and 3-aminomethyl-cyclopropylmethyl arylcarboxamide.

8. The polynucleotide cleavage agent according to claim 1 which is selected from the group consisting of 3-aminomethyl-2,2-difluoro-cyclopropylmethyl 9-anthracenecarboxylate, 3-aminomethyl-2,2-difluoro-cyclopropylmethyl 9-anthracenecarboxamide and 3-hydroxymethyl-2,2-difluoro-cyclopropylmethyl 9-anthracenecarboxamide.

9. A polynucleotide cleavage agent switched on by photo-irradiation which comprises cyclopropane or 2,2-dihalogeno-cyclopropane ring between "A" unit and "B" unit, and also "C" unit, wherein said "A" unit is an aromatic group having electron withdrawing property and is excited by photo-irradiation, said "B" unit is a hydrophilic functional group and said "C" unit can recognize a DNA sequence.

10. The polynucleotide cleavage agent according to claim 9 which also comprises a spacer molecule.

11. The polynucleotide cleavage agent according to claim 9 wherein said 2,2-dihalogeno-cyclopropane is selected from a group consisting of 2,2-difluoro-, 2,2-dichloro- and 2,2-dibromo-cyclopropanes.

12. The polynucleotide cleavage agent according to claim 9 wherein said aromatic group is an arylcarboxylic moiety.

13. The polynucleotide cleavage agent according to claim 12 wherein said arylcarboxylic moiety is selected from a group consisting of anthracene-, pyren-, fluorene-, naphthalimide, quinoline, quinoxaline, anthraquinone and flavin-carboxylic moieties.

14. The polynucleotide cleavage agent according to claim 9 wherein said hydrophilic functional group is selected from a group consisting of amino-, alkylamino-, carbamoyl, hydroxyl and ammonium groups.

15. The polynucleotide cleavage agent according to claim 9 where said "A" unit is an arylcarboxylic moiety selected from a group consisting of anthracene-, pyren-, fluorene-, naphthalimide, quinoline, quinoxaline, anthraquinone and flavin-carboxylic moieties, and said "B" unit is a hydrophilic functional group selected from a group consisting of amino-, alkylamino-, carbamoyl, hydroxyl and ammonium groups.

16. The polynucleotide cleavage agent according to claim 9 wherein said "C" unit is a nucleic acid or a peptide nucleopeptide.

17. The polynucleotide cleavage agent according to claim 9 which is selected from a group consisting of 3-aminomethyl-2,2-difluoro-cyclopropylmethyl arylcarboxylate, 3-aminomethyl-cyclopropylmethyl arylcarboxylate, 3-aminomethyl-2,2-difluoro-cyclopropylmethyl arylcarboxamide and 3-aminomethyl-cyclopropylemethyl arylcarboxamide.

18. The polynucleotide cleavage agent according to claim 9 which is selected from a group consisting of 3-aminomethyl-2,2-difluoro-cyclopropyl methyl 9-anthracene-carboxylate, 3-aminomethyl-2,2-difluoro-cyclopropyl-methyl 9-anthracenecarboxamide, and 3-hydroxymethyl-2,2-difluoro-cyclopropyl methyl 9-anthracenecarboxamide.

19. A method of cleaving or decomposing a polynucleotide which comprises contacting said polynucleotide with a polynucleotide cleavage agent according to claim 1 or 9 and then photo-irradiating to cleave said polynucleotide.

20. A compound selected from a group consisting of 3-aminomethyl-2,2-difluoro-cyclopropylmethyl 9-anthracene-carboxylate, 3-aminomethyl-2,2-difluoro-cyclopropyl-methyl 9-anthracenecarboxamide and 3-hydroxymethyl-2,2-difluoro-cyclopropylmethyl 9-anthracenecarboxamide.

* * * * *